United States Patent
Kim et al.

(10) Patent No.: US 9,976,186 B2
(45) Date of Patent: May 22, 2018

(54) METHOD FOR DETECTING GENES SENSITIVE TO HIGH-LEVEL IONIZING RADIATION, AND GENE DETECTED BY THE METHOD

(75) Inventors: Hee Sun Kim, Uijeongbu (KR); Seung Jin Choi, Seoul (KR); Moo Hyun Choi, Seoul (KR); Jin Jong Bong, Seoul (KR); Seok Cheol Shin, Seoul (KR)

(73) Assignee: KOREA HYDRO & NUCLEAR POWER CO., LTD., Gyeongju-si (KR)

( * ) Notice: Subject to any disclaimer, the term of this patent is extended or adjusted under 35 U.S.C. 154(b) by 446 days.

(21) Appl. No.: 14/399,952

(22) PCT Filed: May 17, 2012

(86) PCT No.: PCT/KR2012/003899
§ 371 (c)(1),
(2), (4) Date: Nov. 9, 2014

(87) PCT Pub. No.: WO2013/168842
PCT Pub. Date: Nov. 14, 2013

(65) Prior Publication Data
US 2016/0355883 A1    Dec. 8, 2016

(30) Foreign Application Priority Data
May 10, 2012   (KR) .................. 10-2012-0049588

(51) Int. Cl.
*C12Q 1/68*   (2018.01)
(52) U.S. Cl.
CPC ......... *C12Q 1/6886* (2013.01); *C12Q 1/6883* (2013.01); *C12Q 2600/158* (2013.01)
(58) Field of Classification Search
CPC ............................................. C12Q 2600/158
See application file for complete search history.

(56) References Cited

FOREIGN PATENT DOCUMENTS

| KR | 10-0541529 B1 | 1/2006 |
| KR | 10-0957055 B1 | 5/2010 |

OTHER PUBLICATIONS

GenBank Accession No. NM_008904.2, publicly available Apr. 24, 2011.*
GenBank Accession No. NM_007981.3, publicly available Apr. 24, 2011.*
GenBank Accession No. NM_010719.5, publicly available May 5, 2011.*
GenBank Accession No. NM_009127.4, publicly available Apr. 30, 2011.*
GenBank Accession No. NM_024450.2, publicly available Mar. 11, 2011.*
Pusztai and Hess. Clinical trial design for microarray predictive marker discovery and assessment. Annals of Oncology, vol. 15, pp. 1731-1737, 2004.*
Pearce et al., "Enhancing CD8 T Cell memory by Modulating Fatty Acid Metabolism," Nature, Jul. 2, 2009, pp. 103-107, vol. 460, No. 7251.
NCBI GenBank Accession No. NM_008904.2, May 24, 2009.
NCBI GenBank Accession No. NM_007981.3, Sep. 21, 2005.
NCBI GenBank Accession No. NM_010719.5, Feb. 14, 2006.
NCBI GenBank Accession No. NM_009127.4, Apr. 28, 2009.
NCBI GenBank Accession No. Nm 024450.2, Feb. 3, 2006.
Shin et al., "Life Span and Thymic Lymphoma Incidence in High- and Low-Dose-Rate Irradiated ADR/J Mice and Commonly Expressed Genes," Radiation Research, Sep. 2010, pp. 341-346, vol. 174, No. 3.
Roudkenar et al., "Gene Expression Profiles in Mouse Live Cells after Exposure to Different Types of Radiation," J. Radiat. Res., Jan. 2008, pp. 29-40, vol. 49.
Iwakawa et al., "Mouse Research models for individual radiosensitivity: individual variance and strain variance," J. Jpn. Soc. ther. Radio. Oncol., 2005, pp. 141-47, vol. 17.
Shin et al., "Differential expression of immune-associated cancer regulatory genes in low-versus high-dose-rate irradiated ADR/J mice", Genomics, Jun. 2011, vol. 97, No. 6, pp. 358-363.
NCBI GenBank Accession No. NM_008904.1, Jan. 4, 2000.
NCBI GenBank Accession No. NM_007981.3, Oct. 3, 2009.
NCBI GenBank Accession No. NM_010719.1, Jan. 25, 2000.
Liu et al., "Transcriptional coactivator PGC-1α integrates the mammalian clock and energy metabolism," Nature, May 24, 2007, pp. 477-481, vol. 447, Nature Publishing Group.
Cormio et al., "The PGC-1α-dependent pathway of mitochondrial biogenesis is upregulated in type I endometrial cancer," Biochem. Biophus. Res. Comm., Oct. 25, 2009, pp. 1182-1185, vol. 390, Elsevier Inc.
Richards et al., "Fatty acid transport protein 1 and long-chain acyl coenzyme A synthetase 1 interact in adipocytes," J. Lipid Res., 2006, pp. 665-672, vol. 47, American Society for Biochemistry and Molecular Biology, Inc.
Parkes et al., "Overexpression of acyl-CoA synthetase-1 increases lipid deposition in hepatic (HepG2) cells and rodent liver in vivo," Am. J. Physiol. Endocrinol Metab., May 16, 2006, pp. E737-E744, vol. 291, The American Physiological Society.
Holm et al., "Hormone-Sensitive Lipase: Sequence, Expression, and Chromosomal Localization to 19 cent-q13.3," Science, Sep. 16, 1988, pp. 1503-1506, vol. 241.

(Continued)

*Primary Examiner* — Jennifer Dunston
(74) *Attorney, Agent, or Firm* — Im IP Law; C. Andrew Im

(57) ABSTRACT

A method for detecting genes sensitive to high-level ionizing radiation and genes detected by the method. More specifically, genes sensitive to high-level ionizing radiation discovered in a carcinogenic entity and verified in a normal entity are detected, by subjecting a cancerous AKR/J mouse and a normal ICR mouse to high-level radiation. Thymus is collected therefrom and fatty acid metabolism-related genes are classified via microarray processing of the thymus. The genes are amplified and the levels of gene expression are measured. Thus, a gene having a specific reaction to radiation can be accurately detected by preventing the interference of confounding variables.

4 Claims, 2 Drawing Sheets

(56) References Cited

OTHER PUBLICATIONS

Greenberg et al., "Stimulation of Lipolysis and Hormone-sensitive Lipase via the Extracellular Signal-regulated Kinase Pathway," J. Biol. Chem., Nov. 30, 2001, pp. 45456-45461, vol. 276, No. 48.
Larsson et al., "Lack of cholesterol mobilization in islets of hormone-sensitive lipase deficient mice impairs insulin secretion," Biochem. Biophys. Res. Comm., Sep. 18, 2008, pp. 558-562, vol. 376, Elsevier Inc.
Ntambi et al., "Regulation of stearoyl-CoA desaturases and role in metabolism," Prog. Lipid Res., 2004, pp. 91-104, vol. 43, Elsevier Ltd.
Scaglia et al., "Inhibition of StearoylCoA Desaturase-1 Inactivates Acetyl-CoA Carboxylase and Impairs Proliferation in Cancer Cells: Role of AMPK," PloS One, Aug. 27, 2009, pp. e6812:1-14, vol. 4, issue 8.

\* cited by examiner

METHOD FOR DETECTING GENES SENSITIVE TO HIGH-LEVEL IONIZING RADIATION, AND GENE DETECTED BY THE METHOD

REFERENCE TO AN ELECTRONIC SEQUENCE LISTING

The contents of the electronic sequence listing (seq.txt, Size: 2 kilobytes; and Date of Creation: Oct. 21, 2014) is herein incorporated by reference in its entirety.

TECHNICAL FIELD

The present invention relates to a method for detecting genes sensitive to a high level of ionizing radiation and genes detected by the method, and more particularly, to a method for detecting genes sensitive to a high level of ionizing radiation, the method including irradiating cancer-induced mice and normal mice with a high level of radiation, and screening fatty acid metabolism-related genes, which are observed commonly in the normal mice and the cancer-induced mice, from the thymi of the mice.

BACKGROUND ART

With an increase in the industrial and medical use of radiation, various studies on the effects of radiation on the human body have been conducted, and particularly, cancer therapy with radiation has received attention. It is known that high doses of ionizing radiation cause DNA damage, genetic modification, and diseases, including cancer, but a radiation dose of 200 mGy or less and a radiation dose rate of 6 mGy/hr or less inhibit cancer development by activating immune responses.

In general, studies on the relationship between radiation and cancer development, particularly gene responses to radiation, have been conducted, but confounding factors have significantly affected the results to reduce the reliability of the results. However, most studies conducted to date could not explain various responses, which occur in the cells, tissues and organs of the body in the body stage, because these studies were performed using gene-modified cell lines or cancer cell lines. In other words, because gene responses were evaluated using general mice, a variety of genes were expressed, and because cancer development was not limited to a specific organ, it was difficult to analyze gene responses.

In prior art methods that use cells for cancer research, genes were modified, or cancer cells lacking p53 that is important in cancer development were irradiated. For this reason, there was a problem in that the results could not be applied to individuals, because they did fundamentally differ from the responses of normal cells. To overcome this problem, studies on the effects of radiation on cancer development have been conducted using mice having a gene similarity of 95% or more with humans. However, cancer incidence in general mice is very low, and thus a variety of mouse models for cancer research have been used.

In the prior art, a variety of methods were used to screen fatty acid metabolism-related genes sensitive to ionizing radiation. However, fatty acid metabolism-related genes disclosed in the present invention are not yet known as genes sensitive to a high level of ionizing radiation. Technologies prior to the identification of the profile of genes according to the present invention are as follows.

(1) Ppargc1a is known as a member of biorhythm regulator and known to play an important role in biorhythm and energy metabolism (Liu C et. al., Nature 2007; 447:477-481).

(2) Ppargc1a activated mitochondrial biosynthesis in type 1 endometrial cancer (Cormio A et. al., Biochem Biophus Res Commum 2009; 390: 1182-1185).

(3) The interaction between Acsl1 and FATP1 in adipocytes increased the uptake of long-chain fatty acids (Richards M R et. al., J Lipid Res 2006; 47: 665-72).

(4) Injection of Acsl1 inserted into adenovirus increased the accumulation of adipose in C57BL6 mice and Wistar rats (Parkes H A et. al., Am J Physiol Endocrinol Metab 2006; 291:E737-744).

(5) Lipe is known as a rate limiting enzyme for diacylglycerol and cholesteryl ester hydrolysis in adipocytes (Holm C et. al., Science 1998; 241: 1503-1506).

(6) Activation of EPK signaling in adipocytes stimulated lypolysis through HSL phosphorylation (Greenberg A S et. al., J Biol Chem 2001; 276: 45456-454561).

(7) Inhibition of HSL expression in pancreatic islets reduced insulin secretion (Larsson, 2008).

(8) Scd is known as a rate limiting enzyme that is involved in the synthesis of unsaturated fatty acids from saturated fatty acids (Ntambi J M, Miyazaki M, Prog Lipid Res 2004; 43: 91-104; Flowers M T, Ntambi J M, Curr Opin Lipidol 2008; 19: 248-256).

(9) Cancer cells activated Scd1 to regulate the synthesis of sugar-linked lipids. However, when the function of Scd1 was abnormal, acetyl-CoA carboxylase activity was inhibited by AMPK, and the synthesis and accumulation of saturated fatty acids were inhibited (Scaglia N et. al. (2009) PLoS One 4: e6812).

Accordingly, the present inventors have identified the profile of fatty acid metabolism-related genes sensitive to a high level of ionizing radiation, thereby completing the present invention.

DISCLOSURE

Technical Problem

It is an object of the present invention to provide a method for detecting a gene sensitive to a high level of ionizing radiation, and a gene detected by the method.

Technical Solution

In order to accomplish the above object, the present invention provides a method for detecting a gene that is sensitive to a high level of ionizing radiation and is identified in a cancer-induced individual and verified using a normal individual, the method including the steps of: I) irradiating an AKR/J mouse and an ICR mouse with a high level of radiation; II) extracting thymi from the AKR/J mice and the ICR mice; III) subjecting the thymi to microarray analysis; IV) selecting a fatty acid metabolism-related gene from the microarray analysis; and V) amplifying the gene and measuring the expression level of the gene.

The present invention also provides a marker for diagnosing a radiation-sensitive or radiation-induced cancer, the marker including the nucleotide sequence of a fatty acid metabolism-related gene selected from the group consisting of Ppargc1a (NM_008904), Acsl1 (NM_007981), Lipe (NM_010719), Scd1 (NM_009127) and Scd3 (NM_024450), which are involved in worsening of thymic cancer.

The present invention also provides a kit for diagnosing a radiation-sensitive or radiation-induced cancer, the kit including the above marker.

The present invention also provides a microarray for diagnosing a radiation-sensitive or radiation-induced cancer, the microarray including the above marker.

The present invention also provides a method for screening a drug for treating or inhibiting a radiation-sensitive or radiation-induced cancer, the method including the steps of: I) irradiating a mammal having thymic cancer with radiation; II) bringing a test substance into contact with a thymic tissue extracted from the irradiated mammal; and III) measuring, from the thymic tissue, a change in the expression of a fatty acid metabolism-related gene selected from the group consisting of Ppargc1a (NM_008904), Acsl1 (NM_007981), Lipe (NM_010719), Scd1 (NM_009127) and Scd3 (NM_024450), which are involved in worsening of thymic cancer.

Hereinafter, the present invention will be described in detail.

Many studies on the effects of radiation on cancer development among the effects of radiation on the human body have been conducted, but it was difficult to explain various responses of the body to radiation (responses of genes to radiation), because these studies were performed using cancer cells, gene-modified cell lines or general mice. Particularly, the profile of fatty acid metabolism-related genes sensitive to ionizing radiation in individuals has not yet been identified, and the functions of these genes have not been explained. Accordingly, the present invention is intended to (1) identify the profile of fatty acid metabolism-related genes that are expressed specifically in thymus and sensitive to a high level of radiation, and analyze the functions of the genes, after irradiating a high level (0.8 Gy/min) of radiation (cancer development stimulator) to normal ICR mice and AKR/J mice that develop thymic cancer, and 2) diagnose the stage of development of thymic cancer using the profile of fatty acid metabolism-related genes.

The present invention provides a method for detecting a gene that is sensitive to a high level of ionizing radiation and is identified in a cancer-induced individual and verified using a normal individual, the method including the steps of: I) irradiating an AKR/J mouse and an ICR mouse with a high level of radiation; II) extracting thymi from the AKR/J mice and the ICR mice; III) subjecting the thymi to microarray analysis; IV) selecting a fatty acid metabolism-related gene from the microarray analysis; and V) amplifying the gene and measuring the expression level of the gene.

In the inventive method for detecting a gene sensitive to a high level of ionizing radiation, irradiating the mouse with the high level of radiation is preferably performed by irradiating gamma radiation (Cs-137) at a dose rate of 0.8 Gy/min to a final dose of 4.5 Gy. The method according to the present invention is preferably used for preparation of a kit for diagnosing thymic cancer, evaluation of the degrees of progression and treatment of cancer in a cancer patient, evaluation of the relationship between radiation exposure of industrial and medical workers and cancer development, evaluation of the causal relation between radiation and cancer development, biological evaluation of radiation exposure dose, or evaluation of the degrees of development and progression of thymic cancer caused by a high level of radiation.

In addition, the inventive method for detecting a gene sensitive to a high level of ionizing radiation, the cancer is preferably thymic cancer, and extracting the thymi in step II) is preferably performed at a time point when the mouse starts to die of the cancer.

Furthermore, in the inventive method for detecting a gene sensitive to a high level of ionizing radiation, the fatty acid metabolism-related gene is preferably selected from the group consisting of Ppargc1a (NM_008904), Acsl1 (NM_007981), Lipe (NM_010719), Scd1 (NM_009127) and Scd3 (NM_024450). Preferably, the Ppargc1a (NM_008904) gene is amplified using primers having sequences set forth in SEQ ID NOS: 1 and 2; the Acsl1 (NM_007981) gene is amplified using primers having sequences set forth in SEQ ID NOS: 3 and 4; the Lipe (NM_010719) gene is amplified using primers having sequences set forth in SEQ ID NOS: 5 and 6; the Scd1 (NM_009127) gene is amplified using primers having sequences set forth in SEQ ID NOS: 7 and 8; and the Scd3 (NM_024450) gene is amplified using primers having sequences set forth in SEQ ID NOS: 9 and 10.

In step IV☐ of selecting the fatty acid metabolism-related gene from the microarray analysis, a gene overexpressed or underexpressed in the cancer-induced individual after irradiation compared to in the cancer-induced individual before irradiation is detected by microarray analysis, and then verified using primers having sequences of SEQ ID NOS: 1 to 10, and the overexpressed or underexpressed gene is identified by performing a search for the function thereof. The microarray analysis is described in the Examples below, and a search for the function of the gene was performed in the Examples through the DAVID bioinformatics database and (apps1.niaid.nih.gov) and the PubMed database (www.ncbi.n1m.nih.gov), but is not limited thereto.

As used herein, "gene sensitive to a high level of radiation" refers to a gene that is differentially overexpressed or underexpressed in a cancer-induced individual after radiation compared to before irradiation. In other words, the gene refers to a gene whose expression pattern is changed by stimulation with radiation, and it may be a target gene associated with a specific cancer, that is, an oncogene or a tumor suppressor gene. When this cancer-specific gene is detected, a molecular mechanism for radiotherapy of cancer patients can be established, which can contribute to an increase in the effect of radiotherapy, and a platform for the development of agents or methods for treating cancer at the biomolecular level can be provided by screening novel oncogenes or tumor suppressor genes and regulating the expression thereof.

The present invention also provides a marker for diagnosing a radiation-sensitive or radiation-induced cancer, the marker including the nucleotide sequence of a gene selected from the group consisting of Ppargc1a (NM_008904), Acsl1 (NM_007981), Lipe (NM_010719), Scd1 (NM_009127) and Scd3 (NM_024450), which are involved in worsening of thymic cancer.

The present invention also provides a kit for diagnosing a radiation-sensitive or radiation-induced cancer, the kit including the above marker.

The present invention also provides a microarray for diagnosing a radiation-sensitive or radiation-induced cancer, the microarray including the above marker.

The present invention also provides a method for screening a drug for treating or inhibiting a radiation-sensitive or radiation-induced cancer, the method including the steps of: I) irradiating a mammal having thymic cancer with radiation; II) bringing a test substance into contact with a thymic tissue extracted from the irradiated mammal; and III) measuring, from the thymic tissue, a change in the expression of a fatty acid metabolism-related gene selected from the group consisting of Ppargc1a (NM_008904), Acsl1 (NM_007981), Lipe (NM_010719), Scd1 (NM_009127) and Scd3 (NM_024450), which are involved in worsening of thymic cancer.

In the present invention, AKR/J mice (models for thymic cancer research) and healthy ICR mice were irradiated with a high level (0.8 Gy/min) of gamma radiation (Cs-137), and thymi were extracted from the mice at a time point (day 100) when the AKR/J mice started to die of thymic cancer. The extracted thymi were analyzed by microarray analysis, and then fatty acid metabolism-related genes that responded sensitively to the high level of radiation (0.8 Gy/min) were selected through the DAVID bioinformatics database, and subjected to nucleic acid amplification, and the expression levels thereof were measured.

As a result, five genes (Ppargc1a, Acsl1, Lipe, Scd1 and Scd3), which responded sensitively to the high level of radiation (0.8 Gy/min) and are important in fatty acid metabolism, were screened in the present invention, and the functions of the fatty acid metabolism-related genes (Ppargc1a, Acsl1, Lipe, Scd1 and Scd3) that responded sensitively to the high level of radiation (0.8 Gy/min) were elucidated. In addition, the fatty acid metabolism-related genes responding sensitively to the high level of radiation could be consistently observed by extracting thymi at day 100 when death caused by thymic cancer was observed.

Therefore, the present invention may be used to: (1) identify the profile of genes for development of a kit for diagnosing thymic cancer; (2) identify a marker for evaluating the relation of cause and effect of cancer development in industrial and medical workers who live in environments having a low level of radiation; (3) identify the profile of genes for information, which enable the diagnosis of cancer development in cancer patients and allow a cancer therapeutic method to be established; (4) identify a marker for evaluating the causal relation between radiation exposure and the development of thymic cancer; 5) identify a novel gene marker that may be widely used for biological evaluation of a high level of radiation exposure; and (6) understand ionizing radiation-sensitive fatty acid metabolism signaling that may be used as a target therapy for a high level of radiation exposure.

Advantageous Effects

The method for detecting a gene sensitive to a high level of ionizing radiation as described above may be used to establish the profile of fatty acid metabolism-related marker genes sensitive to a high level of radiation in order to prepare a kit for diagnosing thymic cancer, and may provide a fatty acid metabolism-related marker gene sensitive to a high level of radiation, which can be used to evaluate the degrees of progression and progression of cancer in cancer patients. Also, the method according to the present invention may provide a fatty acid metabolism-related marker gene sensitive to a high level of radiation, which can be used to evaluate the relationship between the radiation exposure of industrial and medical workers and cancer development. Further, it may provide a fatty acid metabolism-related marker sensitive to a high level of radiation, which can be used to evaluate the causal relation between radiation and cancer development. In addition, it may provide a novel marker that can be used for biological evaluation of radiation exposure dose. Also, it may provide a fatty acid metabolism-related marker that can be used to evaluate the degrees of development and progression of thymic cancer caused by a high level (0.8 Gy/min) of radiation.

MODE FOR INVENTION

Figure 1:
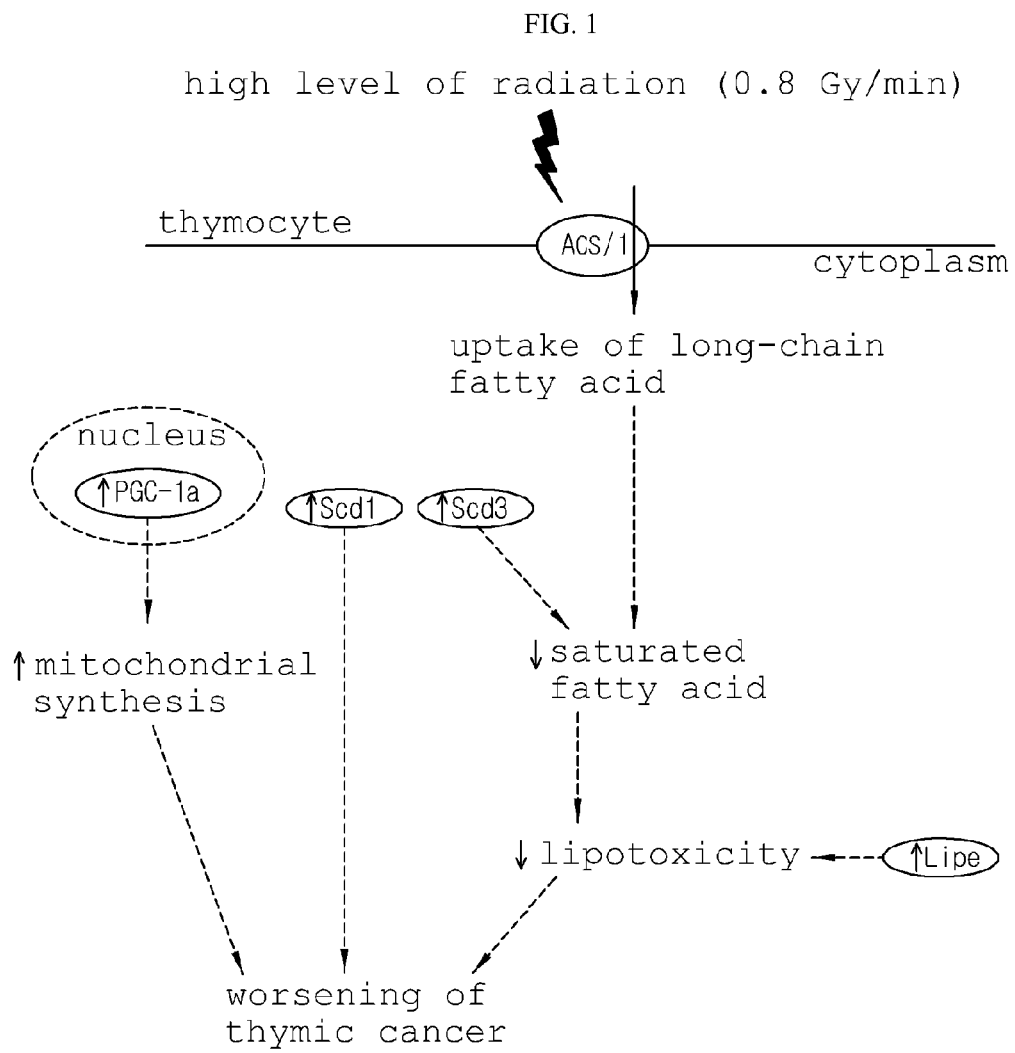
FIG. 1 schematically shows the functions of fatty acid metabolism-related genes (Ppargc1a, Acsl1, Lipe, Scd1 and Scd3) that worsen thymic cancer upon irradiation with a high level (0.8 Gy/min) of radiation.

Hereinafter, the present invention will be described in further detail with reference to examples. It is to be understood, however, that these examples are for illustrative purposes only and are not intended to limit the scope of the present invention.

Example 1

6-Week-old female AKR/J mice (models for thymic cancer research) and 6-week-old female ICR mice were purchased from SLC Co., Ltd. (Japan). A high level of radiation ($^{137}$Cs) was irradiated to the AKR/J mice using a gamma-ray generator (IBL 147C, CIS bio international, France) at a dose rate of 0.8 Gy/min so as to reach a final dose of 4.5 Gy. After completion of irradiation with the high level of radiation, the mice were transferred into a sterilized housing system shielded from radiation, and were housed therein for 100 days while the observation of development of thymic cancer was performed. For gene analysis, under the same experimental conditions, normal mice (ICR mice) housed separately from the AKR/J mice were irradiated with a high level of radiation (0.8 Gy/min). After 100 days, thymi were extracted from the mice and frozen rapidly in liquid nitrogen, after which gene analysis was performed.

Example 2: Microarray and Gene Analysis

Using mouse models (AKR/J mice) for cancer research, irradiated in Example 1, fatty acid metabolism-related genes sensitive to a high level of radiation (0.8 Gy/min) were screened. The screened genes were verified using normal mice (ICR mice). Specifically, fatty acid metabolism-related genes that responded to a high level of radiation (0.8 Gy/min) specifically in the thymi of the AKR/J and ICR mice irradiated with the high level of radiation were screened, and their functions were analyzed. Analysis was performed using the DAVID bioinformatics database, a quantitative nucleic acid amplification technique, and the statistical program SAS (ANOVA and t-test).

To confirm the results, the genes were subjected to nucleic acid amplification. Specifically, the thymi extracted from the AKR/J and ICR mice irradiated with the high level of radiation (0.8 Gy/min) were microarrayed, and fatty acid metabolism-related genes that responded sensitively to the high level of radiation were amplified using the primers shown in Table 1 below in order to measure the expression levels thereof.

TABLE 1

| Gene No. | Gene name | Forward (5'->3') | Reverse (5'->3') |
|---|---|---|---|
| NM_008904 | Ppargc1a | ACCGTAAATCTGCGGGATGATGGA | AGTCAGTTTCGTTCGACCTGCGTA |
| NM_007981 | Acsl1 | AAGCCGGTCTGAAGCCATTTGAAC | TCGCCTTCAGTGTTGGAGTCAGAA |
| NM_010719 | Lipe | ATCCCAGGCTCACAGTTACC | TCCTTCCCGTAGGTCATAGG |
| NM_009127 | Scd1 | CTCCTGCTGATGTGCTTCAT | AAGGTGCTAACGAACAGGCT |
| NM_024450 | Scd3 | CTGCTGATGTGCTTCATCCT | AGCACCACAGCGTATCTCAG |

After irradiation of the AKR/J and ICR mice with the high level of radiation (0.8 Gy/min), the mice were housed, and thymi were extracted from the mice at a time point (day 100) when the AKR/J mice started to die of thymic cancer. The extracted thymi were microarrayed, and fatty acid metabolism-related genes that responded sensitively to the high level of radiation were selected, and then subjected to nucleic acid amplification, and the expression levels thereof were measured. As a result, it was shown that, in the mice irradiated with the high level of radiation, fatty acid metabolism-related genes (Ppargc1a, Acsl1, Lipe, Scd1 and Scd3) responded sensitively to the high level of radiation. The results are shown in Table 2 below.

TABLE 2

| | | Microarray | | Quantitative nucleic amplification | |
|---|---|---|---|---|---|
| Gene No. | Gene name | ICR mice | AKR/ J mice | ICR mice | AKR/ J mice |
| NM_008904 | Ppargc1a | 0.6 | 1.4 | 4.5 ± 1.5* | 2.4 ± 1.6 |
| NM_007981 | Acsl1 | 1.0 | 1.3 | 4.8 ± 1.7 | 2.6 ± 1.3 |
| NM_010719 | Lipe | 1.5 | 1.2 | 2.7 ± 0.9 | 1.5 ± 0.3 |
| NM_009127 | Scd1 | 0.9 | 3.7 | 20.7 ± 15.9 | 3.7 ± 4.6 |
| NM_024450 | Scd3 | 0.9 | 1.9 | 1.4 ± 0.4 | 3.0 ± 1.0 |

*Expression fold value ± SD

FIG. 1 schematically shows the functions of fatty acid metabolism-related genes (Ppargc1a, Acsl1, Lipe, Scd1 and Scd3) that worsen thymic cancer due to irradiation with a high level of radiation (0.8 Gy/min). As can be seen therein, the high level of radiation increased the expression of Acsl1, resulting in an increase in the uptake of long-chain fatty acids into thymocytes. Increases in the expression levels of Scd1 and Scd3 inhibited the accumulation of saturated fatty acids, and reduced lipotoxicity by increasing the expression of Lipe. In addition, the expression of Ppargc1a was increased to increase mitochondrial synthesis and worsen thymic cancer.

Figure 2:
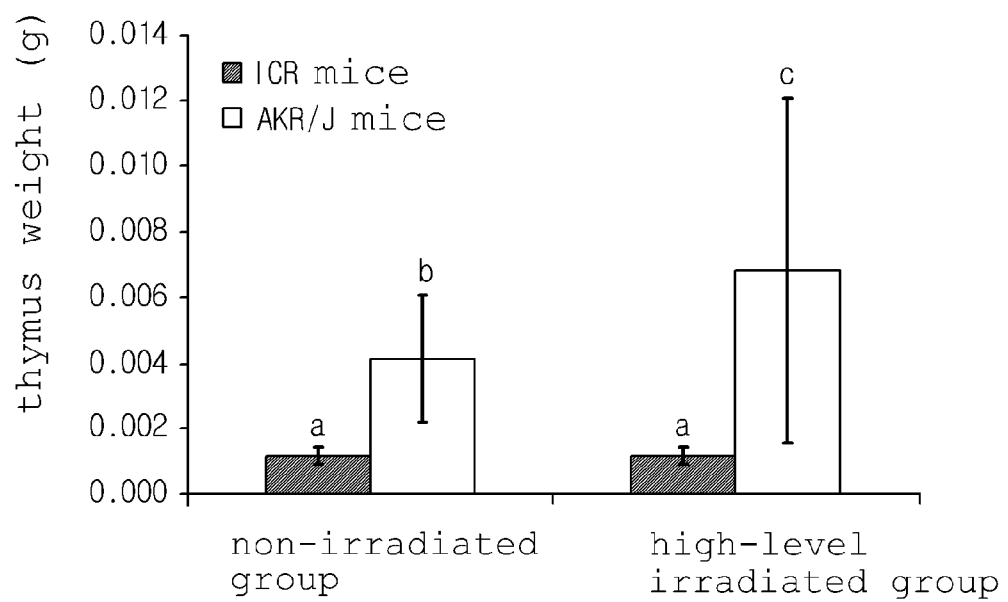
FIG. 2 is a graph showing the results obtained by irradiating AKR/J mice with a high level (0.8 Gy/min) of radiation and measuring the weight of thymi of the mice at a time point (day 100) when the mice started to die of thymic cancer during their housing, in order to analyze the responses of fatty acid metabolism-related genes sensitive to radiation based on the thymus weight.

FIG. 2 shows the weight of thymi extracted at a time point (day 100) when AKR/J mice started to die of thymic cancer during their housing after AKR/J and ICR mice were irradiated with a high level of radiation (0.8 Gy/min). According to the present invention, fatty acid metabolism-related genes that respond sensitively to a high level of radiation can be consistently measured by extracting thymi in an early stage of cancer development in which mice start to die of thymic cancer, and comparing the weights of the extracted thymi.

The invention claimed is:

1. A method for detecting a gene sensitive to a level of ionizing radiation, the method comprising the steps of:
   irradiating a cancer-induced AKR/J mouse and an ICR mouse with a gamma radiation at a dose rate of 0.8 Gy/min to a final dose of 4.5 Gy;
   extracting thymi from the AKR/J mouse and the ICR mouse;
   subjecting the thymi to a microarray analysis;
   selecting a Scd3 gene as a fatty acid metabolism-related gene from the microarray analysis; and
   amplifying the Scd3 gene and measuring an expression level of the gene.

2. The method of claim 1, wherein the cancer is thymic cancer.

3. The method of claim 1, further comprising the step of extracting the thymi a time point when the mouse starts to die of the cancer.

4. The method of claim 1, wherein the step of amplifying the Scd3 gene uses primers having sequences set forth in SEQ ID NOS: 9 and 10.

* * * * *

SEQUENCE LISTING

<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: Ppargc1a Forward primer

<400> SEQUENCE: 1
accgtaaatc tgcgggatga tgga                                    24

<210> SEQ ID NO 2
<211> LENGTH: 24
<212> TYPE: DNA
<213> ORGANISM: Artificial Sequence
<220> FEATURE:
<223> OTHER INFORMATION: Ppargc1a Bacward primer

<400> SEQUENCE: 2
agtcagtttc gttcgacctg cgta                                    24

<210> SEQ ID NO 3
<211> LENGTH: 24
<212> TYPE: DNA
<213> ORGANISM: Artificial Sequence
<220> FEATURE:
<223> OTHER INFORMATION: Acsl1 Forward primer

<400> SEQUENCE: 3
aagccggtct gaagccattt gaac                                    24

<210> SEQ ID NO 4
<211> LENGTH: 24
<212> TYPE: DNA
<213> ORGANISM: Artificial Sequence
<220> FEATURE:
<223> OTHER INFORMATION: Acsl1 Backward primer

<400> SEQUENCE: 4
tcgccttcag tgttggagtc agaa                                          24

<210> SEQ ID NO 5
<211> LENGTH: 20
<212> TYPE: DNA
<213> ORGANISM: Artificial Sequence
<220> FEATURE:
<223> OTHER INFORMATION: Lipe Forward primer

<400> SEQUENCE: 5
atcccaggct cacagttacc                                               20

<210> SEQ ID NO 6
<211> LENGTH: 20
<212> TYPE: DNA
<213> ORGANISM: Artificial Sequence
<220> FEATURE:
<223> OTHER INFORMATION: Lipe Backrward primer

<400> SEQUENCE: 6
tccttcccgt aggtcatagg                                               20

<210> SEQ ID NO 7
<211> LENGTH: 20
<212> TYPE: DNA
<213> ORGANISM: Artificial Sequence
<220> FEATURE:
<223> OTHER INFORMATION: Scd1 Forward primer

<400> SEQUENCE: 7
ctcctgctga tgtgcttcat                                               20

<210> SEQ ID NO 8
<211> LENGTH: 20
<212> TYPE: DNA
<213> ORGANISM: Artificial Sequence
<220> FEATURE:
<223> OTHER INFORMATION: Scd1 Backward primer

<400> SEQUENCE: 8
aaggtgctaa cgaacaggct                                               20

<210> SEQ ID NO 9
<211> LENGTH: 20
<212> TYPE: DNA
<213> ORGANISM: Artificial Sequence
<220> FEATURE:
<223> OTHER INFORMATION: Scd3 Forward primer

<400> SEQUENCE: 9
ctgctgatgt gcttcatcct                                               20

<210> SEQ ID NO 10
<211> LENGTH: 20
<212> TYPE: DNA
<213> ORGANISM: Artificial Sequence
<220> FEATURE:

```
<223> OTHER INFORMATION: Scd3 Backward primer

<400> SEQUENCE: 10
agcaccacag cgtatctcag                                              20
```